US012667454B2

(12) United States Patent
Wu

(10) Patent No.: US 12,667,454 B2
(45) Date of Patent: Jun. 30, 2026

(54) URINARY INCONTINENCE AUTOMATIC CONTROL SYSTEM HAVING MULTI-POINT ALTERNATE SWITCHING FUNCTION, AND IN-VIVO MACHINE THEREOF

(71) Applicant: Beijing Mikang Medical Technology Co., Ltd., Beijing (CN)

(72) Inventor: Shuangchen Wu, Beijing (CN)

(73) Assignee: Beijing Mikang Medical Technology Co., Ltd., Beijing (CN)

( * ) Notice: Subject to any disclaimer, the term of this patent is extended or adjusted under 35 U.S.C. 154(b) by 1074 days.

(21) Appl. No.: 17/778,716

(22) PCT Filed: Nov. 20, 2020

(86) PCT No.: PCT/CN2020/130332
§ 371 (c)(1),
(2) Date: May 20, 2022

(87) PCT Pub. No.: WO2021/098812
PCT Pub. Date: May 27, 2021

(65) Prior Publication Data
US 2023/0016009 A1      Jan. 19, 2023

(30) Foreign Application Priority Data

Nov. 22, 2019    (CN) .......................... 201911155574.5

(51) Int. Cl.
*A61F 2/00*          (2006.01)
*A61B 17/122*       (2006.01)
*A61F 5/00*          (2006.01)

(52) U.S. Cl.
CPC .......... *A61F 2/0036* (2013.01); *A61B 17/122* (2013.01); *A61F 5/0059* (2013.01); *A61F 2250/0002* (2013.01)

(58) Field of Classification Search
CPC .............................. A61B 17/12; A61F 5/0003
See application file for complete search history.

(56) References Cited

U.S. PATENT DOCUMENTS

| | | | | |
|---|---|---|---|---|
| 10,653,544 | B2 * | 5/2020 | Forsell | .................... A61F 5/003 |
| 2004/0122527 | A1 * | 6/2004 | Imran | ....................... A61F 2/04 |
| | | | | 623/23.67 |

(Continued)

FOREIGN PATENT DOCUMENTS

| | | |
|---|---|---|
| CN | 1698552 A | 11/2005 |
| CN | 101896137 A | 11/2010 |

(Continued)

OTHER PUBLICATIONS

Chinese Office Action mailed on Nov. 4, 2020, for Chinese Patent Application No. 201911155574.5, 23 total pages (with English Translation).

(Continued)

*Primary Examiner* — Charles A Marmor, II
*Assistant Examiner* — Marc D. Honrath
(74) *Attorney, Agent, or Firm* — Cooley LLP

(57) ABSTRACT

Disclosed are an automatic control system for urinary incontinence with a function of multi-point switching in turn and an intracorporeal apparatus (200) thereof. The intracorporeal apparatus (200) is completely implanted in a body. The intracorporeal apparatus (200) comprises an intracorporeal microcontroller (220) and urethral blockers (230), the intracorporeal microcontroller (220) being configured to control the urethral blockers (230) to block and unblock the urethra. The intracorporeal apparatus (200) comprises at least two urethral blockers (230) provided at different locations on the urethra, i.e., a first urethral blocker (230*a*) and a second urethral blocker (230*b*), and the intracorporeal microcon- (Continued)

troller (220) is configured to control the at least two urethral blockers (230) to block and unblock the urethra in turn.

26 Claims, 7 Drawing Sheets

(56) References Cited

U.S. PATENT DOCUMENTS

| | | | |
|---|---|---|---|
| 2006/0142636 A1 | 6/2006 | Meretei | |
| 2007/0167672 A1 | 7/2007 | Dlugos et al. | |
| 2007/0249893 A1 | 10/2007 | Krumme | |
| 2009/0247817 A1 | 10/2009 | Forsel | |
| 2011/0015738 A1 | 1/2011 | Vaingast et al. | |
| 2012/0095288 A1 | 4/2012 | Snow et al. | |
| 2014/0378749 A1 | 12/2014 | Taylor et al. | |
| 2016/0074196 A1 | 3/2016 | Forsell | |
| 2017/0079760 A1 | 3/2017 | Newman et al. | |
| 2019/0329044 A1 | 10/2019 | Forsell | |

FOREIGN PATENT DOCUMENTS

| | | | | |
|---|---|---|---|---|
| CN | 103298426 A | 9/2013 | | |
| CN | 104548338 A | 4/2015 | | |
| CN | 105228563 A | 1/2016 | | |
| CN | 105392446 A | 3/2016 | | |
| CN | 107771069 A | 3/2018 | | |
| CN | 110840507 A | 2/2020 | | |
| EP | 2 409 668 A1 | 1/2012 | | |
| JP | H-03-57448 A | 3/1991 | | |
| JP | 2002-536116 A | 10/2002 | | |
| JP | 2011-509099 A | 3/2011 | | |
| JP | 2012-500712 A | 1/2012 | | |
| JP | 2016-509918 A | 4/2016 | | |
| WO | WO-2007122505 A2 * | 11/2007 | ............ | A61F 2/004 |
| WO | WO-2010/042047 A1 | 4/2010 | | |
| WO | WO-2019/106402 A1 | 6/2019 | | |

OTHER PUBLICATIONS

Chinese Office Action mailed on Mar. 31, 2021, for Chinese Patent Application No. 201911155574.5, 26 total pages (with English Translation).

International Search Report mailed on Feb. 23, 2021, for PCT Application No. PCT/CN2020/130332, 12 total pages (with English Translation).

Written Opinion of the International Searching Authority mailed on Feb. 23, 2021, for PCT Application No. PCT/CN2020/130332, 13 total pages (with English Translation).

Extended European Search Report mailed on Nov. 29, 2023, for EP Application No. 20 891 200.6, 8 total pages.

* cited by examiner

URINARY INCONTINENCE AUTOMATIC CONTROL SYSTEM HAVING MULTI-POINT ALTERNATE SWITCHING FUNCTION, AND IN-VIVO MACHINE THEREOF

RELATED APPLICATIONS

The present application is a U.S. National Phase Application, filed under 35 U.S.C. § 371, of International Application No. PCT/CN2020/130332, filed Nov. 20, 2020, which claims priority to, and the benefit of, Chinese Patent Application No. 201911155574.5, filed Nov. 22, 2019, the entirety of the disclosure of each of which is incorporated herein by reference.

FIELD OF THE INVENTION

The present disclosure relates to an automatic control system for urinary incontinence with a function of multi-point switching in turn. The present disclosure also relates to an intracorporeal apparatus for the automatic control system for urinary incontinence.

BACKGROUND OF THE INVENTION

Urinary incontinence is common in the elderly population and there are some treating methods available, but still a great number of patients have no effective means for treatment and have to rely on palliative measures such as continuous urethral catheterization or urinal pads and diaper pants, thus leading to a serious decline in the quality of life of patients and also causing great troubles to their families. Therefore, clinically there is a need to develop new devices for urinary incontinence treatment.

An artificial urethral sphincter device has been developed clinically, which has the advantage of capable of restoring control of urination while allowing urination through the normal urethra without affecting the anatomy of the sphincter and nearby tissues, so patients can achieve an improved quality of life. However, existing artificial urethral sphincter devices also have some shortcomings. For example, the existing artificial urethral sphincter devices are low in reliability, e.g., they may excessively compress urethral tissues in particular circumstances, causing damage to the urethral tissues. In addition, such an existing artificial urethral sphincter device uses a manually operated pump, which is implanted subcutaneously in a private part such as the scrotum or labia majora of the body, and the manually operated pump needs to be pressed manually during a urination operation, which leads to inconvenience in operation and control and results in a short service life of the entire device.

SUMMARY OF THE INVENTION

In view of at least one shortcoming in the existing artificial urinary sphincter devices, one of the objects of the present disclosure is to provide an automatic control system for urinary incontinence that is convenient to operate and control. Another object of the present disclosure is to provide an automatic control system for urinary incontinence that is highly reliable.

To this end, in an aspect of the present disclosure, an intracorporeal apparatus for controlling urinary incontinence is provided, which is completely implanted in a body, the intracorporeal apparatus including an intracorporeal microcontroller and urethral blockers, the intracorporeal microcontroller being configured to control the urethral blockers to block and unblock the urethra, wherein the intracorporeal apparatus comprises at least two urethral blockers provided at different locations on the urethra, and the intracorporeal microcontroller is configured to control the at least two urethral blockers to block and unblock the urethra in turn.

In one embodiment, the urethral blocker includes a clipping mechanism, which achieves clipping by a hydraulic pressure, an electromagnetic force, a mechanical force generated by a motor, a force generated by a shape memory alloy when the temperature changes, or a force generated by a bimetallic strip when the temperature changes.

In one embodiment, the intracorporeal apparatus further includes at least one pump, a solenoid valve set and a reservoir bag, and each of the urethral blockers includes a C-shaped bag, the intracorporeal microcontroller being electrically connected with the at least one pump and the solenoid valve set, respectively, the reservoir bag being connected with the C-shaped bag through a connecting tube via the at least one pump and the solenoid valve set, and the intracorporeal microcontroller controlling the at least one pump and the solenoid valve set so that liquid is filled into and released from the C-shaped bags of the urethra blocks in turn.

In one embodiment, the intracorporeal apparatus further includes a control box, and the at least one pump, the solenoid valve set and the intracorporeal microcontroller are accommodated within the control box.

In one embodiment, the intracorporeal microcontroller controls the at least one pump and the solenoid valve set so that the C-shaped bag of one of the urethral blockers is filled with liquid each time, and after the filling is completed, liquid in the C-shaped bag of the urethral blocker filled with liquid last time is released, and the C-shaped bag filled with liquid this time is kept in a filled state for a predetermined time.

In one embodiment, the solenoid valve set includes a master solenoid valve and a plurality of urethral blocker solenoid valves for each of the urethral blockers respectively, wherein first ends of the urethral blocker solenoid valves are respectively connected with the corresponding urethral blockers; second ends of the urethral blocker solenoid valves are both connected with a first end of the master solenoid valve; a second end of the master solenoid valve is connected with a liquid inlet and outlet port of the reservoir bag; a first end of the pump is connected with the second ends of the urethral blocker solenoid valves; and a second end of the pump is connected with the liquid inlet and outlet port of the reservoir bag.

In one embodiment, the urethral blocker further includes a support ring located on the outer side of the C-shaped bag, the support ring being configured to open by elastic deformation when the pressure in the support ring is above a threshold.

In one embodiment, the support ring is configured to maintain its shape unchanged or recover its original shape before elastic deformation when the pressure in the support ring is less than or equal to the threshold.

In one embodiment, the support ring is configured to maintain a constant elastic force during the elastic deformation.

In one embodiment, the support ring is made of a material with a superelastic effect or made of a combination of at least two spring plates, wherein the material is preferably a nickel-titanium alloy.

In one embodiment, the support ring includes a first segment, a second segment, a third segment and a fourth segment that are connected successively, wherein the second segment and the third segment form a C-shaped main body portion of the support ring; the first segment is bent from one end of the second segment in a direction opposite to a bending direction of the second segment; and the fourth segment is bent from one end of the third segment in a direction opposite to a bending direction of the third segment, wherein the first segment and the fourth segment first come close to each other from the end of the second segment and the end of the third segment, respectively, until contact with each other, and then go away from each other.

In one embodiment, the reservoir bag is provided with a replenishing liquid injection valve having an elastic puncture surface.

In one embodiment, a needle stopper plate is provided on a side opposite to the puncture surface.

In one embodiment, the intracorporeal microcontroller is configured to control the at least one pump and the solenoid valve set to release all urethral blockers to unblock the urethra if the supply voltage is detected to be abnormal and is still abnormal after given time.

In one embodiment, the intracorporeal microcontroller is configured to control the at least one pump and the solenoid valve set to immediately stop filling the urethral blockers with the liquid when abnormality of the supply voltage is detected.

In one embodiment, the intracorporeal microcontroller is configured to resume normal control of the at least one pump and the solenoid valve set if abnormality of the supply voltage is detected and the supply voltage returns to normal after given time.

In one embodiment, the intracorporeal apparatus further includes a protection circuit independent of the intracorporeal microcontroller, the protection circuit being triggered to control the at least one pump and the solenoid valve set to release all urethral blockers to unblock the urethra if a signal received by the intracorporeal apparatus from the outside of the body is at a low potential for more than set time.

In one embodiment, the power supply circuit of the intracorporeal apparatus includes an energy storage element.

In one embodiment, each solenoid valve has an energy storage capacitor.

In one embodiment, a pressure sensor is provided between the C-shaped bag and the support ring.

In one embodiment, the intracorporeal microcontroller is electrically connected with the pressure sensor to collect a pressure detection value detected by the pressure sensor in real time, and when the pressure detection value exceeds a maximum pressure set value, the intracorporeal microcontroller controls the at least one pump and the solenoid valve set to release the corresponding urethral blocker to unblock the urethra.

In one embodiment, the intracorporeal microcontroller is electrically connected with the pressure sensor to collect a pressure detection value detected by the pressure sensor in real time, and when the pressure detection value in the urethral blocker in a filled state is less than a minimum pressure set value, the intracorporeal microcontroller controls the at least one pump and the solenoid valve set to fill the C-shaped bag of the urethral blocker with the liquid.

In one embodiment, the at least one pump 240 has a flow rate of 3 mL/min-40 mL/min, and the at least one pump has pressure intensity of 5-120 kPa.

In one embodiment, the intracorporeal apparatus further includes an intracorporeal wireless transmission module, the intracorporeal microcontroller being electrically connected with the intracorporeal wireless transmission module, the extracorporeal wireless transmission module being configured to be capable of obtaining electric energy wirelessly from the outside of the body and capable of bidirectional wireless communication with the outside of the body.

In a second aspect of the present disclosure, an automatic control system for urinary incontinence with a function of multi-point switching in turn is provided, the automatic control system for urinary incontinence including an extracorporeal apparatus located outside the body and the intracorporeal apparatus according to the first aspect of the present disclosure.

In one embodiment, the extracorporeal apparatus includes an extracorporeal wireless transmission module, an extracorporeal microcontroller, and a power module, the power module being configured to supply power to the extracorporeal wireless transmission module and the extracorporeal microcontroller, the extracorporeal microcontroller being electrically connected with the extracorporeal wireless transmission module, wherein the extracorporeal wireless transmission module is wirelessly coupled with the intracorporeal wireless transmission module, and the extracorporeal wireless transmission module is configured to transmit electric energy to the intracorporeal wireless transmission module, and the extracorporeal wireless transmission module and the intracorporeal wireless transmission module are capable of bidirectional wireless communication with each other.

In one embodiment, the extracorporeal apparatus further includes a display and control module, which is electrically connected with the extracorporeal microcontroller to display operation information of the automatic control system for urinary incontinence and to input operating commands and parameters.

In one embodiment, the display and control module includes a touch screen.

In one embodiment, the extracorporeal apparatus further includes an alarm module, which is electrically connected with the extracorporeal microcontroller to emit an alarm signal indicating system abnormality to a user.

In one embodiment, the extracorporeal apparatus further includes a Bluetooth module and/or a WIFI module, the Bluetooth module and/or the WIFI module being configured to be capable of communicating with a cloud server or a mobile terminal.

BRIEF DESCRIPTION OF THE DRAWINGS

These and other features, aspects and advantages of the present disclosure will become better understood when the following detailed description is read with reference to the accompanying drawings, in which same reference signs denote same parts, wherein.

DETAILED DESCRIPTION OF THE EMBODIMENTS

The present disclosure will be described below with reference to the accompanying drawings, wherein the drawings illustrate a number of embodiments of the present disclosure. It should be understood, however, that the present disclosure may be presented in many different ways and is not limited to the embodiments described below; in fact, the embodiments described below are intended to make the present disclosure more complete and to fully illustrate the scope of protection of the present disclosure to those skilled in the art. It should also be understood that the embodiments disclosed herein can be combined in various ways to provide additional embodiments.

It should be understood that the wording in the specification is only used to describe specific embodiments and not intended to limit the present disclosure. Unless otherwise defined, all terms (including technical and scientific terms) used in the specification have meanings as generally understood by those skilled in the art. For the sake of brevity and/or clarity, well-known functions or structures may be not described in detail.

The words "include," "comprise" and "contain" used in the specification indicate the presence of a claimed feature, but do not exclude the presence of one or more other features. The word "and/or" used in the specification includes any and all combinations of one or more of relevant listed items.

The term "connected to", "connected with" or similar terms used in the specification are intended to indicate a direct and/or indirect connection.

The system described in the specification may use one or more microcontrollers to receive information and transform the received information to generate an output. The microcontroller may include any type of computing device, computing circuitry, or any type of microcontroller or processing circuitry capable of executing a series of instructions stored in a memory. The microcontroller may include a plurality of microcontrollers and/or a multi-core central processing unit (CPU), and may include any type of microcontroller. The microcontroller may also include a memory to store data and/or algorithms to execute a series of instructions.

Figure 1:
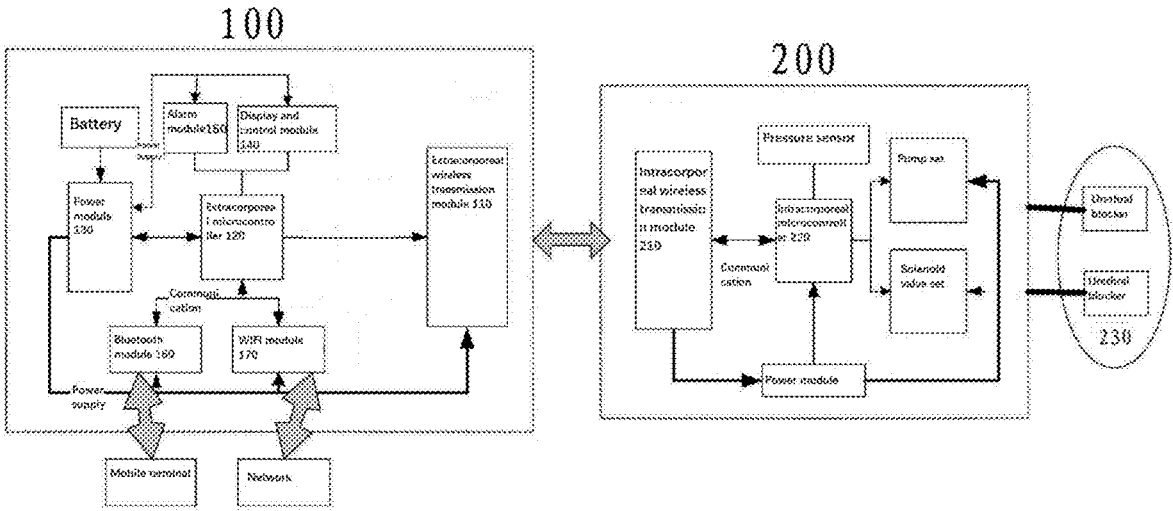
FIG. 1 is a schematic block diagram of an automatic control system for urinary incontinence according to the present disclosure.

FIG. 1 shows a schematic block diagram of an automatic control system for urinary incontinence according to the present disclosure. The automatic control system for urinary incontinence of the present disclosure is used to treat urinary incontinence due to sphincter relaxation. The automatic control system for urinary incontinence includes an extracorporeal apparatus 100 and an intracorporeal apparatus 200. The intracorporeal apparatus 200 may be completely implanted inside a body and may be configured to accomplish a main function of an artificial urethral sphincter. The extracorporeal apparatus 100 may be located outside the body, and may be configured to supply power to the intracorporeal apparatus and communicate with the intracorporeal apparatus, and may also accomplish intracorporeal apparatus control and information display and alarm functions.

As shown in FIG. 1, the extracorporeal apparatus 100 may include an extracorporeal wireless transmission module 110, an extracorporeal microcontroller 120, and a power module 130. The power module 130 is electrically connected with the extracorporeal wireless transmission module 110 and the extracorporeal microcontroller 120, to supply power to the extracorporeal wireless transmission module 110 and the extracorporeal microcontroller 120. The power module 130 may be powered by a battery or by any other suitable external power source. The extracorporeal microcontroller 120 is electrically connected with the extracorporeal wireless transmission module 110. The intracorporeal apparatus 200 may include an intracorporeal wireless transmission module 210, an intracorporeal microcontroller 220, and urethral blockers 230. The intracorporeal microcontroller 220 is electrically connected with the intracorporeal wireless transmission module 210. The intracorporeal microcontroller 220 is configured to control the urethral blockers 230 to block and unblock the urethra. The extracorporeal wireless transmission module 110 is wirelessly coupled with the intracorporeal wireless transmission module 210. The extracorporeal wireless transmission module 110 is configured to transmit electric energy to the intracorporeal wireless transmission module 210, thereby powering the intracorporeal wireless transmission module 200. The extracorporeal wireless transmission module 110 and the intracorporeal wireless transmission module 210 are capable of bidirectional wireless communication with each other to transmit information.

The extracorporeal wireless transmission module 110 may include a drive circuit, an information read/write circuit of the extracorporeal apparatus, and an extracorporeal coil Wp1. The intracorporeal wireless transmission module 210 may include an intracorporeal coil Ws1, an extracorporeal information readout circuit of the intracorporeal apparatus, an intracorporeal information write circuit of the intracorporeal apparatus, and a power supply circuit. The drive circuit is electrically connected with the extracorporeal coil Wp1 and is configured to output an alternating electrical signal to the extracorporeal coil Wp1. The extracorporeal coil Wp1 is configured to generate an alternating magnetic field. The intracorporeal coil Ws1 is configured to generate an induced electromotive force based on the alternating magnetic field. The power supply circuit is electrically connected with the intracorporeal coil Ws1 to provide stable electric energy for the intracorporeal apparatus. The power supply circuit may also be electrically connected with an energy storage element such as a rechargeable battery. The information read/write circuit of the extracorporeal apparatus, the extracorporeal information readout circuit of the intracorporeal apparatus, and the intracorporeal information write circuit of the intracorporeal apparatus are configured to modulate information to be communicated to an energy-transmitting electromagnetic wave for transmission and to demodulate received signals into readable information, thereby bidirectionally transmitting information between the intracorporeal apparatus 100 and the extracorporeal apparatus 200. Each of the extracorporeal coil Wp1 and the intracorporeal coil Ws1 includes a magnet, such as a low-eddy-current magnet, so that the extracorporeal coil Wp1 and the intracorporeal coil Ws1 can be positioned with respect to each other using attractive forces of the magnets, to ensure good coupling of the two coils.

Thus, when the extracorporeal apparatus 100 supplies power to the intracorporeal apparatus 200, the drive circuit drives a current with a certain waveform to pass through the extracorporeal coil to generate an alternating magnetic field, which generates an induced electromotive force on the intracorporeal coil Ws1 coupled with the extracorporeal coil, and after processing such as rectification, filtering and voltage stabilization of the power supply circuit of the intracorporeal apparatus, a stable DC voltage can be provided to other components in the intracorporeal apparatus. During information transmission between the extracorporeal apparatus 100 and the intracorporeal apparatus 200, information to be communicated is modulated to an energy-transmitting electromagnetic wave according to a certain rule so that energy transmission and information transmission are implemented by the same set of electromagnetic transmission coils. This achieves the effects of a simple structure, efficient energy transmission and reliable bidirectional information transmission.

Figure 2:
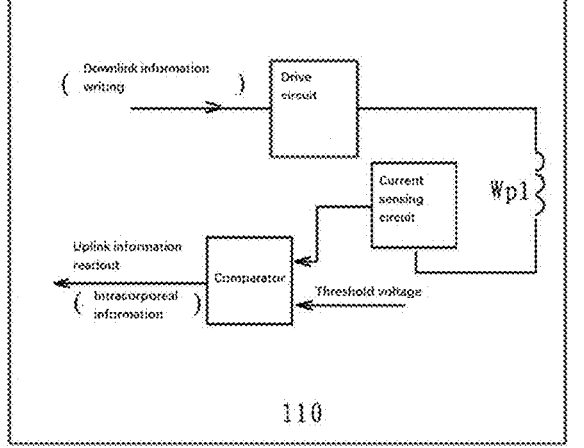
FIG. 2 is a circuit block diagram of an implementation of an extracorporeal wireless transmission module of an extracorporeal apparatus and an intracorporeal wireless transmission module of an intracorporeal apparatus of the automatic control system for urinary incontinence according to the present disclosure.
Figure 2:
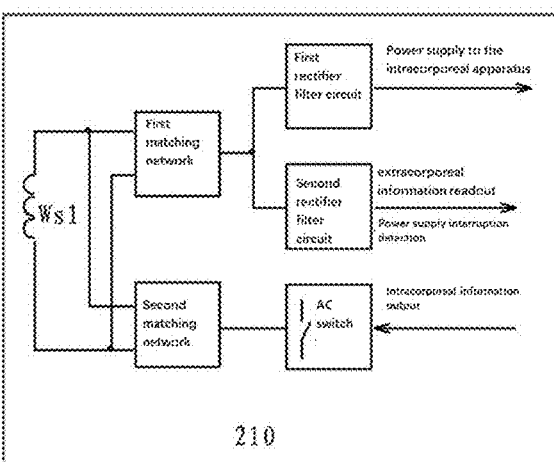

FIG. 2 shows a circuit block diagram of an implementation of the extracorporeal wireless transmission module 110 and the intracorporeal wireless transmission module 210 according to the present disclosure.

In the extracorporeal wireless transmission module 110, Wp1 represents the extracorporeal coil configured to output energy and information to the intracorporeal coil Ws1. The drive circuit outputs an alternating power electrical signal of a certain frequency to the extracorporeal coil Wp1. The information read/write circuit of the extracorporeal apparatus (which may specifically be an intracorporeal information readout circuit of the extracorporeal apparatus) includes a current sensing circuit and a comparator, wherein the current sensing circuit is configured to detect the current of the extracorporeal coil Wp1 and convert the current value into a voltage signal, and the comparator obtains information sent by the intracorporeal apparatus 200 according to two sets of signals of an output voltage from the current sensing circuit and a threshold voltage output from the extracorporeal microcontroller 120. The extracorporeal microcontroller 120 enables/disables the drive circuit at a predetermined communication frequency (much lower than the frequency of the power electrical signal output from the drive circuit) to send information to the intracorporeal apparatus.

In the intracorporeal wireless transmission module 210, Ws1 represents the intracorporeal coil configured to receive the energy sent by the extracorporeal coil Wp1. The AC signal received by the intracorporeal coil Ws1 is converted to a DC voltage through a first matching network and a first rectifier filter circuit with a first time constant to provide electric energy to the intracorporeal apparatus 200. The extracorporeal information readout circuit of the intracorporeal apparatus and the power supply circuit share the first matching network, but a second rectifier filter circuit with a second time constant is used to convert the presence/absence of energy received by Ws1 into a high/low level of a voltage signal which is sent to the intracorporeal microcontroller 220. The first time constant is greater than the second time constant. A signal that changes at the predetermined communication frequency can be parsed to obtain downlink information from the extracorporeal apparatus, and a low level that exceeds a certain duration can be used as a basis for determining the interruption of power supply from the extracorporeal apparatus 100. An AC switch brings the second matching network into conduction with the intracorporeal coil Ws1 according to information output from the intracorporeal microcontroller 220, resulting in a change in equivalent impedance of the corresponding extracorporeal coil Wp1. Using this method, information is transmitted to the extracorporeal apparatus 100. In one embodiment, the first matching network and the second matching network may be impedance matching networks. The impedance matching networks may be circuits with series and parallel reactive elements for impedance matching.

For the power supply from the extracorporeal apparatus 100 to the intracorporeal apparatus 200, an appropriate operating frequency is used, such as an operating frequency of 100 kHz to 4 MHz, to minimize comprehensive losses of the transmission coils and switching elements. Both the intracorporeal coil and the extracorporeal coil achieve impedance matching by connecting appropriate reactive elements (capacitors or inductors) in series and/or parallel to improve transmission efficiency of energy.

For the wireless information transmission between the extracorporeal apparatus 100 and the intracorporeal apparatus 200, an information transmission baud rate much lower than the energy transmission operating frequency is used in order to take into account the requirements of reliable information transmission, electromagnetic compatibility and energy transmission efficiency. For the transmission of information from the extracorporeal apparatus 100 to the intracorporeal apparatus 200.

the drive circuit starts/stops driving of the extracorporeal coil Wp1 at appropriate time, and the intracorporeal apparatus 200 detects the presence/absence of a voltage output from the intracorporeal coil Ws1 to obtain the information according to a preset coding rule. For the transmission of information from the intracorporeal apparatus 200 to the extracorporeal apparatus 100, the equivalent impedance of the extracorporeal coil Wp1 is changed by short-circuiting the intracorporeal coil Ws1 using the AC switch or the AC switch and a matching capacitor at appropriate time, thereby changing the current of the extracorporeal coil Wp1. The transmitted information can be obtained according to a preset coding rule by using the current sensing circuit and the comparator.

The extracorporeal apparatus 100 may also include a display and control module 140, an alarm module 150, a Bluetooth® module 160, and/or a WIFI module. The power module 130 is electrically connected with the display and control module 140, the alarm module 150, the Bluetooth® module 160 and/or the WIFI module 170 to supply power thereto.

The display and control module 140 is electrically connected with the extracorporeal microcontroller 120. The display and control module 140 is configured to display operation information of the automatic control system for urinary incontinence and to input operating commands and parameters. For example, the display and control module 140 can display the remaining battery capacity in real time, and give a prompt for replacement and charging when the capacity reaches a lower limit. The display and control module 140 may include a touch screen. The display and control module 140 may also be composed of a separate display screen and an input device such as a keyboard.

The alarm module 150 is electrically connected with the extracorporeal microcontroller 120. The alarm module 150 is configured to emit an alarm signal indicating system abnormality to a user. The alarm signal may be an acoustic signal and/or an optical signal.

The Bluetooth module 160 and/or the WIFI module 170 is electrically connected to the extracorporeal microcontroller 120. The Bluetooth module 160 and/or the WIFI module 170 is configured to be capable of communicating with a cloud server or a mobile terminal such as a cell phone, to upload system operation, and prompt a patient or caregiver for a urination operation via the mobile terminal, and be capable of monitoring system operation via APP software on the mobile terminal.

In use, when the patient inputs a urination command, the extracorporeal wireless transmission module 110 and the intracorporeal wireless transmission module 210 transmit the urination command to the intracorporeal microcontroller 220, and the intracorporeal microcontroller 220 controls an actuator so that the urethral blocker comes into a released state and urination begins. When the patient inputs a closure command, the wireless communication modules transmit the closure command to the intracorporeal microcontroller 220, and the intracorporeal microcontroller controls the actuator so that the urethral blocker comes into a closed state and urination ends.

The urethral blocker 230 may include a clipping mechanism. The clipping mechanism can achieve clipping of the urethra by various driving methods. For example, the function of clipping the urethra may be accomplished by filling liquid into or releasing liquid from a reservoir bag that is sleeved on the urethra (driving by a hydraulic pressure); the function of clipping the urethra may be accomplished by an action of the clipping mechanism caused by an electromagnet according to an electromagnet principle (driving by an electromagnetic force); the function of clipping the urethra is accomplished by an action of the clipping mechanism caused by a motor (driving by a mechanical force generated by the motor); the function of clipping the urethra is accomplished by using a two-way memory effect of a shape memory alloy, such as a nickel-titanium alloy, that opens/closes when the temperature changes (driving by a force generated by the shape memory alloy when the temperature changes); or the function of clipping the urethra is accomplished by deformation of a bimetallic strip when the temperature changes due to an expansion coefficient difference of metals (driving by a force generated by the bimetallic strip when the temperature changes); or the like.

Figure 3:
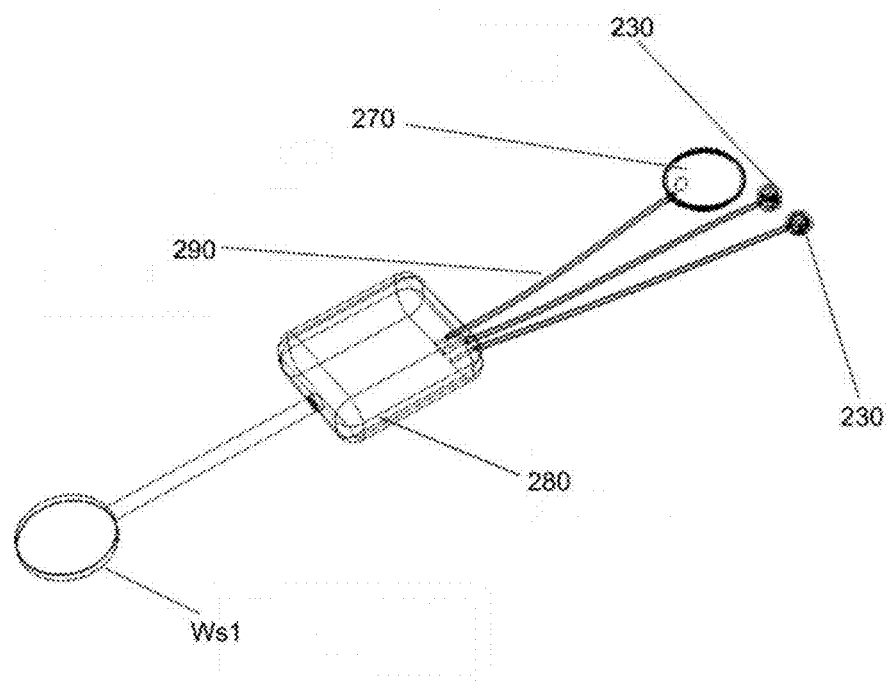
FIG. 3 is a schematic diagram of the intracorporeal apparatus of the automatic control system for urinary incontinence according to the present disclosure.

In one embodiment, at least two urethral blockers 230 may be provided at different locations on the urethra (FIGS. 1 and 3 exemplarily show a case where two urethra blockers are provided). The intracorporeal microcontroller 220 is configured to control the at least two urethral blockers 230 to block the urethra in turn. That is, in a time period, one urethral blocker may be used to block the urethra, while the other urethral blocker(s) is in the released state; and in the next time period, the next urethral blocker is used to block the urethra, while the other urethral blocker(s) is in the released state. Each time period may be set to 10 minutes, 20 minutes, 30 minutes, or any other reasonable length of time, and the intracorporeal microcontroller 220 controls the urethral blockers to automatically perform blocking in turn. In this way, it can effectively avoid poor blood flow and tissue necrosis caused by long-time clipping of a part of the urethra.

The following is detailed description of the configuration of the intracorporeal apparatus and the urethral blockers therein, using an example of clipping the urethra by hydraulic drive, in conjunction with FIGS. 3 to 14.

Figure 4:
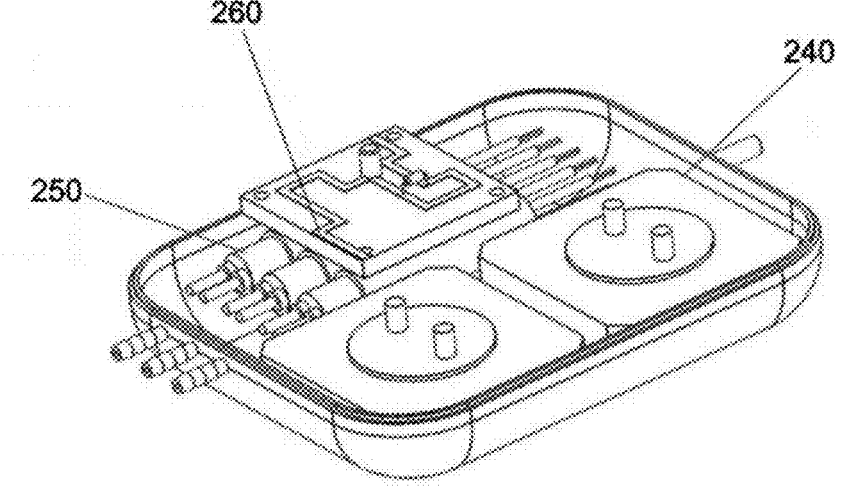
FIG. 4 is an internal structure diagram of a control box of the intracorporeal apparatus of the automatic control system for urinary incontinence according to the present disclosure.

As shown in FIGS. 3 and 4, in addition to the structures described above, the intracorporeal apparatus 200 includes a pump 240 (e.g., a micro pump), solenoid valves 250 (e.g., micro solenoid valves), a circuit board 260 with the intracorporeal microcontroller 220 described above, and a reservoir bag 270. The pump 240 may have a flow rate of 3 mL/min-40 mL/min. The pump 240 may have pressure intensity of 5-120 kPa. The pump 240, the solenoid valves 250 and the circuit board 260 are accommodated within a control box 280. The pump 240 and the solenoid valves 250 are electrically connected with the intracorporeal microcontroller 220 on the circuit board 260 to be controlled by the intracorporeal microcontroller 220. The reservoir bag 270, the urethral blockers 230 and the intracorporeal coil Ws1 described above are provided outside the control box 280. The reservoir bag 270 and the urethral blockers 230 are connected to the pump 240 and the solenoid valves 250 within the control box 280 through corresponding connecting tubes 290. The connecting tubes may be made of silicone or any other suitable material.

Figure 5:
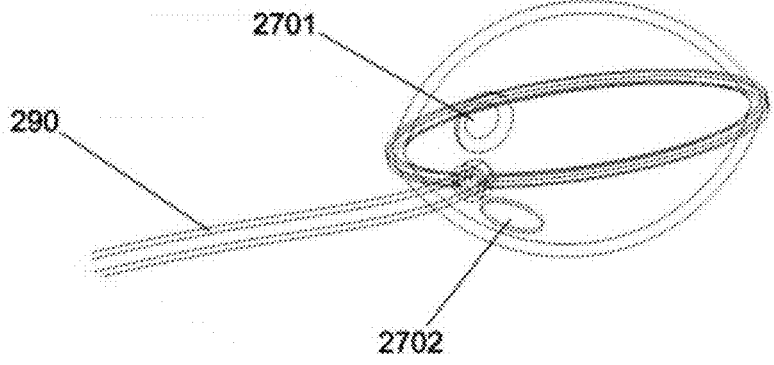
FIG. 5 is a schematic diagram of a reservoir bag of the intracorporeal apparatus of the automatic control system for urinary incontinence according to the present disclosure.

FIG. 5 shows a schematic structure of the reservoir bag 270. The reservoir bag 270 may be made of a silicone rubber material that meets the biologically compatible requirement for implantation into the body. The reservoir bag 270 may be in the shape of an oblate spheroid, and configured to store and provide the liquid required for the urethral blockers. The reservoir bag 270 may be provided with a replenishing liquid injection valve 2701 configured for transdermal injection of replenishing liquid. The replenishing liquid injection valve 2701 may be formed integrally with the reservoir bag 270, or may be connected with the reservoir bag 270 as a separate component through a tube. The replenishing liquid injection valve 2701 may be button-shaped. A puncture surface of the replenishing liquid injection valve 2701 is elastic, and may be, for example, a high-density rubber membrane. This allows restoration of the puncture surface due to its elasticity after a needle is pulled out when liquid replenishment is completed, so the sealing of the reservoir bag 270 can be maintained. A needle stopper plate 2702 may be provided on a side opposite to the puncture surface. The needle stopper plate 2702 may be made of a material that is not easy to puncture to prevent the reservoir bag 270 from being punctured during liquid replenishment. The material is, for example, PET plastic, sheet metal or the like. The reservoir bag 270 has a liquid inlet and outlet port, which is connected to the outside through connecting tubes 290.

Figure 6:
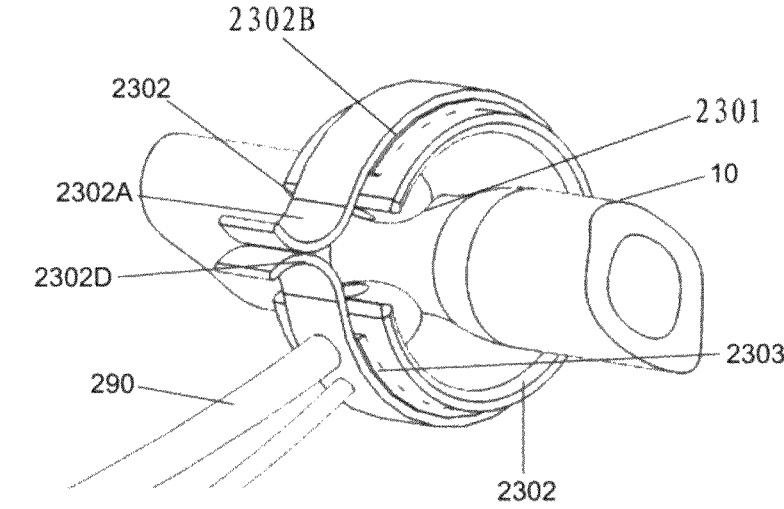
FIG. 6 is a schematic diagram of a first state of a urinary blocker according to the present disclosure.
Figure 7:
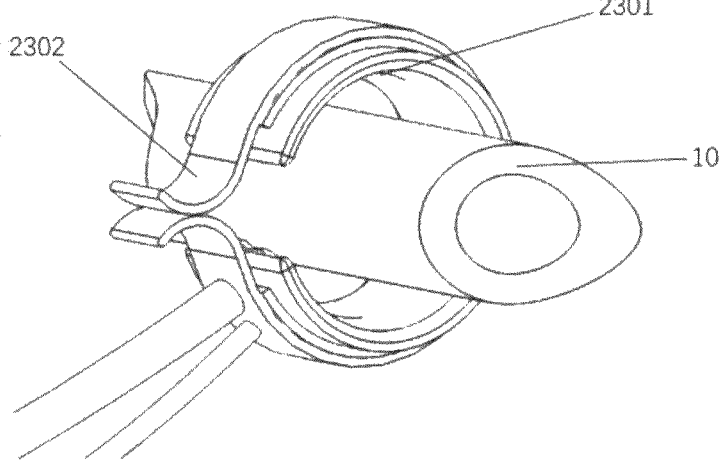
FIG. 7 is a schematic diagram of a second state of the urinary blocker according to the present disclosure.
Figure 8:
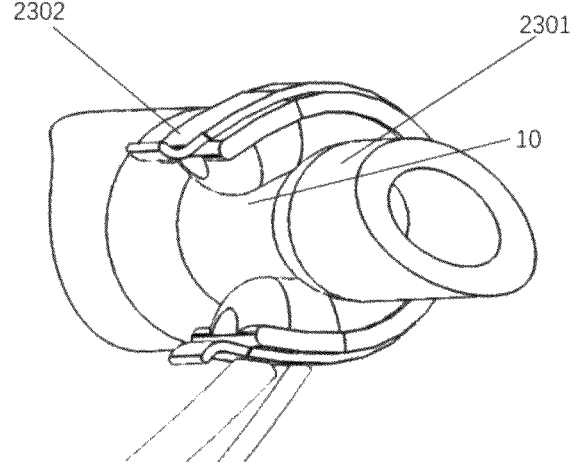
FIG. 8 is a schematic diagram of a third state of the urinary blocker according to the present disclosure.

FIGS. 6 to 8 show another embodiment of the urethral blocker 230. As shown, the urethral blocker 230 includes a C-shaped bag 2301. The C-shaped bag 2301 surrounds the urethra 10 below the bladder neck. The C-shaped bag 2301 forms an unclosed annular bag. The unclosed annular bag allows smooth insertion of a urinary catheter or the like into the urethra in the case where the patient has tissue edema, to avoid urethral injury. The C-shaped bag may be made of silicone or any other suitable material. When the urethral blocker is filled with liquid (e.g., normal saline), the C-shaped bag bulges to raise the pressure and the inner side of the C-shaped bag bulges and compresses the urethra to close the urethra (as shown in FIG. 6); and when the liquid in the urethral blocker is released, the C-shaped bag relaxes and the urethra opens to accomplish a urination operation (as shown in FIG. 7). The C-shaped bag 2301 is connected with the reservoir bag 270 through the connecting tubes 290 via the pump 240 and the solenoid valve 250 to receive the liquid to be filled from the reservoir bag 270 and to release the liquid into the reservoir bag 270. The intracorporeal microcontroller 220 controls the liquid filling and discharge of the C-shaped bag 2301 by controlling the pump 240 and the solenoid valve 250.

In one embodiment, the urethral blocker 230 further includes a support ring 2302 located on the outer side of the C-shaped bag 2301. The support ring 2302 may be configured to open by elastic deformation when the pressure in the support ring 2302 is above a threshold (as shown in FIG. 8) and recovers its original shape before elastic deformation when the pressure in the support ring 2302 is restored below the threshold (as shown in FIGS. 6 and 7). The support ring 2302 may also be configured to maintain its shape unchanged when the pressure in the support ring 2302 is less than or equal to the threshold. In one embodiment, the support ring 2302 is configured to maintain a constant elastic force during the elastic deformation. The threshold may be set to 20 KPa, or for female patients, the threshold may be set to 15 kPa, and for male patients, the threshold may be set to 20 kPa. The threshold may also be set to other reasonable pressure value.

The support ring 2302 may be made of a material with a superelastic effect. The material is, for example, a nickel-titanium alloy or other similar material. The support ring 2302 may also be made of a combination of at least two spring plates. The support ring 2302 and the C-shaped bag 2301 may be molded into one piece from silicone rubber by die casting using a mold.

By using the support ring 2302 as described above, when the pressure intensity of contents (including tissues, the C-shaped bag, etc.) inside the support ring is higher than the threshold due to tissue edema or other reason, as shown in FIG. 8, the support ring elastically deforms and gradually opens up, which leaves a cushion space for the urethra and other tissues to prevent tissue ischemic necrosis and upper urinary tract lesions caused by uncontrollable long-time urethral blockage or excessive bladder pressure. When the pressure decreases, the support ring can automatically return to its position and restore its function.

In one embodiment, the shape of the support ring 2302 is designed as described below. As shown in FIG. 6, the support ring may include a first segment 2302A, a second segment 2302B, a third segment 2302C and a fourth segment 2302D that are connected successively. The second segment 2302B and the third segment 2302C form a C-shaped main body portion of the support ring 2302. The first segment 2302A is bent from one end of the second segment 2302B in a direction opposite to a bending direction of the second segment 2302B, and the fourth segment 2302D is bent from one end of the third segment 2302C in a direction opposite to a bending direction of the third segment 2302C. As shown in FIG. 6, the first segment 2302A and the fourth segment 2302D first come close to each other from the end of the second segment 2302B and the end of the third segment 2302C, respectively, until contact with each other, and then go away from each other. The shape of the support ring 2302 as described above achieves that the support ring can provide constant force support for the urethral blocker in normal times, and tissues can escape smoothly from a mouth portion of the support ring composed of the first segment 2302A and the fourth segment 2302D in the case of an excessive pressure in the ring.

In one embodiment, a pressure sensor 2303 is provided between the C-shaped bag 2301 and the support ring 2302.

The support ring 2302, the C-shaped bag 2301 and the pressure sensor 2303 may be molded into one piece from silicone rubber by die casting using a mold. The pressure sensor 2303 is, for example, a thin film pressure sensor or any suitable pressure sensor. The pressure sensor 2303 is electrically connected with the intracorporeal microcontroller 220 to send a sensed pressure signal to the intracorporeal microcontroller 220. The intracorporeal microcontroller 220 may collect a pressure detection value detected by the pressure sensor 2303 in real time (e.g., every 100 ms).

When the pressure detection value exceeds a maximum pressure set value, the intracorporeal microcontroller 220 controls the pump and the solenoid valve to release the corresponding urethral blocker 230 to unblock the urethra. This improves the safety of the system, thereby ensuring the safety of the patient. Preferably, when the pressure detection value exceeds the maximum pressure set value, the intracorporeal microcontroller 220 sends an alarm signal to the extracorporeal apparatus 100 such that the alarm module 150 of the extracorporeal apparatus 100 alarms, and the intracorporeal microcontroller 220 delays, for a set time (e.g., 10 s), releasing the corresponding urethral blocker 230, thereby giving the patient sufficient preparation time and improving the user experience.

When the pressure detection value in the urethral blocker 230 in a filled state is less than a minimum pressure set value, the intracorporeal microcontroller 220 controls the pump and the solenoid valve to fill the C-shaped bag 2301 of the urethral blocker 230 with the liquid until the pressure in the C-shaped bag 2301 meets the requirement. In this way, by pressure feedback and automatic pressure regulation, the system can operate normally even with a small amount of leakage. The maximum pressure set value and the minimum pressure set value described above may be set in a personalized manner according to conditions of the patient.

Moreover, the system additionally adopts a plurality of safety protection measures to ensure that when the system fails or the power supply fails, all urethral blockers are released, allowing the urethra to be free, to ensure that system failure does not cause upper urinary tract lesions due to long-time urethral closure, thus improving the safety and reliability of the system.

In one embodiment, the intracorporeal microcontroller 220 is configured to detect a supply voltage of the intracorporeal apparatus in real time (e.g., every 100 ms). For example, the intracorporeal microcontroller 220 can determine whether the supply voltage of the intracorporeal apparatus is normal by detecting a potential signal in the extracorporeal information readout circuit of the intracorporeal apparatus. The intracorporeal microcontroller 220 is configured to, when abnormality of the supply voltage of the intracorporeal apparatus is detected, control the pump and the solenoid valves to immediately stop filling the urethral blockers with the liquid, and then continue to detect the supply voltage of the intracorporeal apparatus in real time; if the supply voltage remains abnormal after a set period of time (e.g., 30 s), the intracorporeal microcontroller 220 controls the pump and the solenoid valves to release all urethral blockers to unblock the urethra; if the supply voltage returns to normal after a set period of time (e.g., 30 s), the intracorporeal microcontroller 220 resumes normal control of the pump and the solenoid valves.

To further improve the safety of the system, in one embodiment, the intracorporeal apparatus further includes a protection circuit independent of the intracorporeal microcontroller. The protection circuit is triggered to control the pump and the solenoid valves to release all urethral blockers to unblock the urethra when a signal received by the intracorporeal apparatus 200 from the extracorporeal apparatus 100 is at a low potential (e.g., a "downlink information readout" signal in FIG. 2" is at a "low" level) for more than a set period of time (e.g., longer than a duration of normal information transmission at a low level). This can release the urethral blocker without relying on the microcontroller, but by relying solely on the duration of the "downlink information readout" signal to trigger the protection circuit, thus improving the fault-tolerant redundancy of the system.

To ensure that the control operation of the intracorporeal microcontroller is carried out normally when the supply voltage of the intracorporeal apparatus is abnormal, the power supply circuit of the intracorporeal apparatus 200 is provided with an energy storage element for storing electric energy. To ensure that the solenoid valves have sufficient energy for their release operations, each solenoid valve is provided with an energy storage capacitor. The energy storage capacitor stores energy during normal operation of the solenoid valve. The energy stored in the storage capacitors of the solenoid valves is used only for the release operations of the respective solenoid valves.

As described above, the intracorporeal apparatus 200 may be provided with at least two urethral blockers 230 at different locations on the urethra. In this case, each urethral blocker 230 may have the structures as shown in FIGS. 6 to 8 and as described above. FIGS. 9 to 14 illustrate, by way of example, liquid path connections of the intracorporeal apparatus 200 in the case of an embodiment where two urethral blockers 230a and 230b are provided. However, it may be conceivable for those skilled in the art to provide more than two urethral blockers, in which case it only needs to connect another urethral blocker in parallel at a point O of a liquid path shown in FIG. 9 and connect another solenoid valve in series for another urethral blocker.

Figure 9:
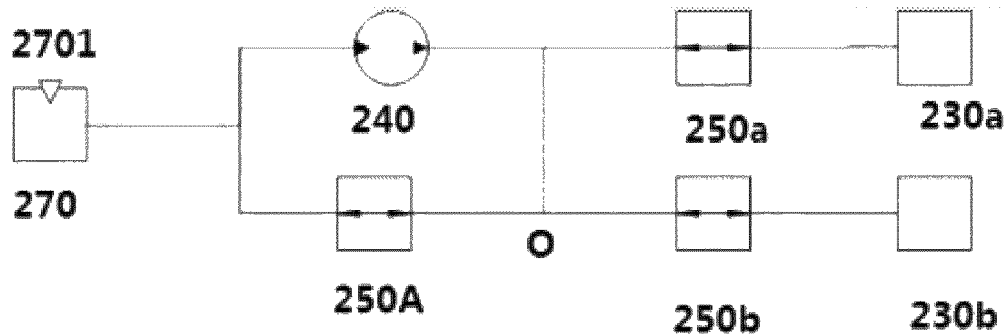
FIG. 9 is a schematic diagram of a liquid path connection of the intracorporeal apparatus of the automatic control system for urinary incontinence according to the present disclosure.

As shown in FIG. 9, the intracorporeal apparatus 200 includes a reservoir bag 270, a pump 240, a master solenoid valve 250A, a first urethral blocker 230a, a second urethral blocker 230b, a first urethral blocker solenoid valve 250a, and a second urethral blocker solenoid valve 250b. A first end of the first urethral blocker solenoid valve 250a is connected with the first urethral blocker 230a, and a first end of the second urethral blocker solenoid valve 250b is connected with the second urethral blocker 230b; respective second ends of the first urethral blocker solenoid valve 250a and the second urethral blocker solenoid valve 250b are connected with a first end of the master solenoid valve 250A; a second end of the master solenoid valve 250A is connected with a liquid inlet and outlet port of the reservoir bag 270; a first end of the pump 240 is connected with the respective second ends of the first urethral blocker solenoid valve 250a and the second urethral blocker solenoid valve 250b; and a second end of the pump 240 is connected with the liquid inlet and outlet port of the reservoir bag 270.

Figure 10:
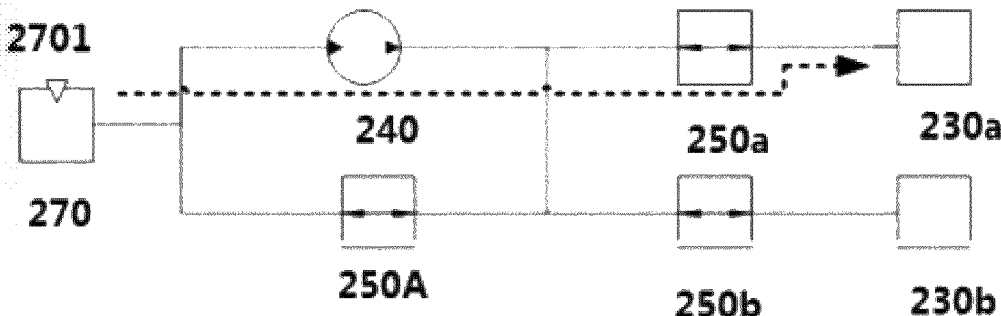
FIG. 10 is a schematic diagram of a first flow state of the liquid path connection shown in FIG. 9.
Figure 11:
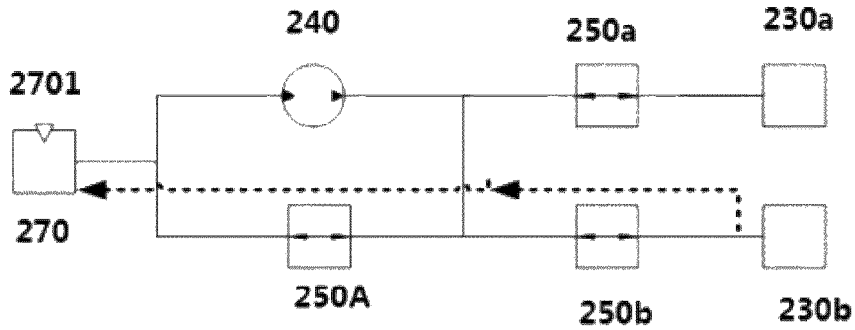
FIG. 11 is a schematic diagram of a second flow state of the liquid path connection shown in FIG. 9.

FIGS. 10 and 11 schematically show principle diagrams of the first urethral blocker 230a clipping the urethra closed and the second urethral blocker 230b releasing the urethra. As shown in the figures, first, the intracorporeal microcontroller 220 controls the pump 240 to be started, the first urethral blocker solenoid valve 250a to be opened, and the master solenoid valve 250A and the second urethral blocker solenoid valve 250b to be closed, at which time the liquid in the reservoir bag 270 is injected into the first urethral blocker 230a through the pump 240 and the first urethral blocker solenoid valve 250a, and the first urethral blocker 230a has continuously increased liquid and expands until completely closing the urethra, at which time the pump 240 stops working, and the first urethral blocker solenoid valve 250a is turned off and maintains the pressure, while the master solenoid valve 250A and the second urethral blocker solenoid valve 250b are opened, and the liquid in the second urethral blocker 230b returns to the reservoir bag 270 due to its own tension, such that the second urethral blocker 230b is released, and the clipping of the urethra is removed.

Figure 12:
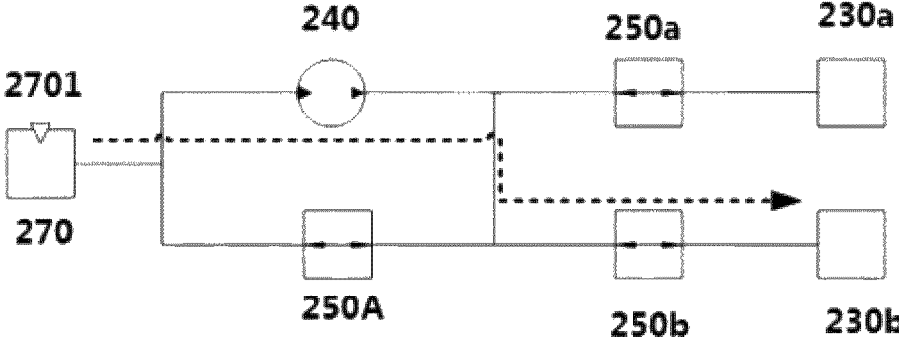
FIG. 12 is a schematic diagram of a third flow state of the liquid path connection shown in FIG. 9.
Figure 13:
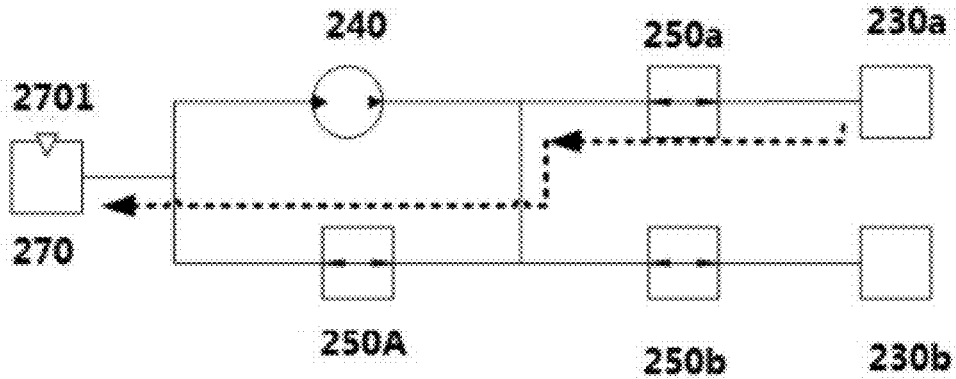
FIG. 13 is a schematic diagram of a fourth flow state of the liquid path connection shown in FIG. 9.

FIGS. 12 and 13 schematically show principle diagrams of the second urethral blocker 230b clipping the urethra closed and the first urethral blocker 230a releasing the urethra. As shown in the figures, first, the intracorporeal microcontroller 220 controls the pump 240 to be started, the second urethral blocker solenoid valve 250b to be opened, and the master solenoid valve 250A and the first urethral blocker solenoid valve 250a to be closed, at which time the liquid in the reservoir bag 270 is injected into the second urethral blocker 230b through the pump 240 and the second urethral blocker solenoid valve 250b, and the second urethral blocker 230b has continuously increased liquid and expands until completely closing the urethra, at which time the pump 240 stops working, and the second urethral blocker solenoid valve 250b is turned off and maintains the pressure, while the master solenoid valve 250A and the first urethral blocker solenoid valve 250a are opened, and the liquid in the first urethral blocker 230a returns to the reservoir bag 270 due to its own tension, such that the first urethral blocker 230a is released, and the clipping of the urethra is removed.

Figure 14:
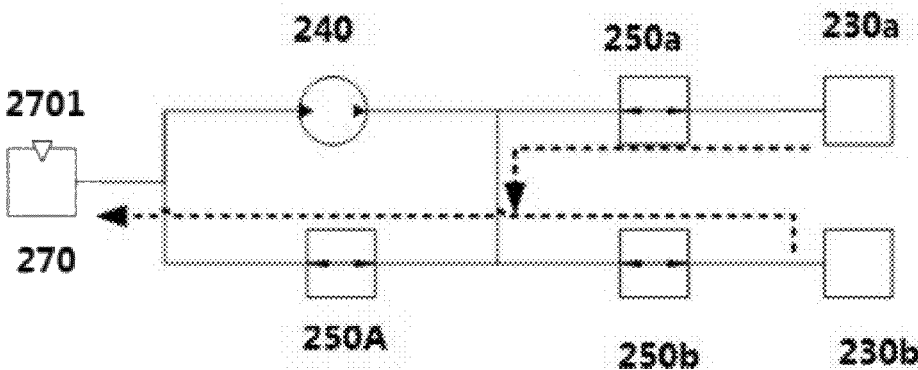
FIG. 14 is a schematic diagram of a fifth flow state of the liquid path connection shown in FIG. 9.

FIG. 14 schematically illustrates a flow state in which the urethral blockers are both released. When urination is needed, the master solenoid valve 250A, the first urethral blocker solenoid valve 250a and the second urethral blocker solenoid valve 250b are all opened, and the liquid in the first urethral blocker 230a and the second urethral blocker 230b flows back through the solenoid valves into the reservoir bag 270 due to their own tension and the internal pressure of the urethra from the bladder, and the urethral blockers release the pressure on the urethra, at which time urine is discharged out of the body through the urethra.

In this way, it can ensure that the two urethral blockers automatically compress the urethra in turn at certain intervals (e.g., 20 minutes) to prevent tissue necrosis due to poor blood flow to the tissues as a result of long-time clipping of the urethra.

INDUSTRIAL APPLICABILITY

The present disclosure can be applied to automatic control of urinary incontinence, and therefore has industrial applicability.

Although only particular embodiments of the present disclosure are illustrated and described herein, those skilled in the art can conceive of a variety of modifications and variations. Therefore, it should be understood that the appended claims are intended to cover all modifications and variations that are within the true spirit of the present disclosure.

The invention claimed is:

1. An intracorporeal apparatus for controlling urinary incontinence, configured to be completely implanted in a body, the intracorporeal apparatus comprising an intracorporeal microcontroller and urethral blockers, the intracorporeal microcontroller being configured to control the urethral blockers to block and unblock a urethra, wherein the intracorporeal apparatus comprises at least two urethral blockers configured to be located at different locations on the urethra, and the intracorporeal microcontroller is configured to control the at least two urethral blockers to block and unblock the urethra in turn;

wherein the intracorporeal apparatus further comprises at least one pump, a solenoid valve set and a reservoir bag, and each of the urethral blockers comprises a C-shaped bag, the intracorporeal microcontroller being electrically connected with the at least one pump and the solenoid valve set, respectively, the reservoir bag being connected with the C-shaped bag through a connecting tube via the at least one pump and the solenoid valve set, and the intracorporeal microcontroller configured to control the at least one pump and the solenoid valve set so as to cause liquid to be filled into and released from the C-shaped bags of the urethral blockers in turn;

wherein the solenoid valve set comprises a master solenoid valve and a plurality of urethral blocker solenoid valves corresponding to each of the urethral blockers respectively, wherein first ends of the plurality of urethral blocker solenoid valves are respectively connected with a liquid inlet and outlet port of the corresponding urethral blockers; second ends of the plurality of urethral blocker solenoid valves are both connected with a first end of the master solenoid valve; a second end of the master solenoid valve is connected with a liquid inlet and outlet port of the reservoir bag; a first end of the at least one pump is connected with the second ends of the plurality of urethral blocker solenoid valves; and a second end of the at least one pump is connected with the liquid inlet and outlet port of the reservoir bag;

wherein the urethral blockers further comprise a support ring located on an outer side of the C-shaped bag, the support ring being configured to open by elastic deformation when a pressure in the support ring is above a threshold;

wherein the support ring comprises a first segment, a second segment, a third segment and a fourth segment that are connected successively, wherein the second segment and the third segment form a C-shaped main body portion of the support ring; the first segment is bent from one end of the second segment in a direction opposite to a bending direction of the second segment; and the fourth segment is bent from one end of the third segment in a direction opposite to a bending direction of the third segment, wherein the first segment and the fourth segment first come close to each other from the end of the second segment and the end of the third segment, respectively, until contact with each other, and then go away from each other.

2. The intracorporeal apparatus according to claim 1, wherein the intracorporeal apparatus further comprises a control box, and the at least one pump, the solenoid valve set and the intracorporeal microcontroller are accommodated within the control box.

3. The intracorporeal apparatus according to claim 1, wherein the urethral blockers comprise a first urethral blocker and a second urethral blocker, the intracorporeal microcontroller is configured to control the at least one pump and the solenoid valve set so that the C-shaped bag of one of the urethral blockers is filled with liquid each time, and after the filling is completed, liquid in the C-shaped bag of the first urethral blocker filled with liquid is released, and the C-shaped bag of the second urethral blocker filled with liquid is kept in a filled state for a predetermined time.

4. The intracorporeal apparatus according to claim 1, wherein the support ring is configured to maintain its shape unchanged or recover its original shape before the elastic deformation when the pressure in the support ring is less than or equal to the threshold.

5. The intracorporeal apparatus according to claim 1, wherein the support ring is configured to maintain a constant elastic force during the elastic deformation.

6. The intracorporeal apparatus according to claim 1, wherein the support ring is made of a material with a superelastic effect or made of a combination of at least two spring plates.

7. The intracorporeal apparatus according to claim 6, wherein the material is a nickel-titanium alloy.

8. The intracorporeal apparatus according to claim 1, wherein the reservoir bag is provided with a replenishing liquid injection valve having an elastic puncture surface.

9. The intracorporeal apparatus according to claim 8, wherein a needle stopper plate is provided on a side opposite to the elastic puncture surface.

10. The intracorporeal apparatus according to claim 1, wherein the intracorporeal microcontroller is configured to control the at least one pump and the solenoid valve set to release all urethral blockers to unblock the urethra if a supply voltage of the intracorporeal apparatus is detected to be abnormal and is still abnormal after a first predetermined time.

11. The intracorporeal apparatus according to claim 10, wherein the intracorporeal microcontroller is configured to control the at least one pump and the solenoid valve set to immediately stop filling the urethral blockers with the liquid when an abnormality of the supply voltage is detected.

12. The intracorporeal apparatus according to claim 10, wherein the intracorporeal microcontroller is configured to resume control of the at least one pump and the solenoid valve set if an abnormality of the supply voltage is detected and the supply voltage returns to normal after a second predetermined time.

13. The intracorporeal apparatus according to claim 10, wherein a power supply circuit of the intracorporeal apparatus further comprises an energy storage element.

14. The intracorporeal apparatus according to claim 10, wherein both the master solenoid valve and the plurality of urethral blocker solenoid valves comprise an energy storage capacitor.

15. The intracorporeal apparatus according to claim 1, wherein the intracorporeal apparatus further comprises a protection circuit independent of the intracorporeal microcontroller, the protection circuit being triggered to control the at least one pump and the solenoid valve set to release all urethral blockers to unblock the urethra if a signal received by the intracorporeal apparatus from outside of the body is at a low potential for more than a set time.

16. The intracorporeal apparatus according to claim 1, wherein a pressure sensor is provided between the C-shaped bag and the support ring.

17. The intracorporeal apparatus according to claim 16, wherein the intracorporeal microcontroller is electrically connected with the pressure sensor to collect a pressure detection value detected by the pressure sensor in real time, and when the pressure detection value exceeds a maximum pressure set value, the intracorporeal microcontroller controls the at least one pump and the solenoid valve set to release the corresponding one of the urethral blockers to unblock the urethra.

18. The intracorporeal apparatus according to claim 16, wherein the intracorporeal microcontroller is electrically connected with the pressure sensor to collect a pressure detection value detected by the pressure sensor in real time, and when the pressure detection value in one of the urethral blockers in a filled state is less than a minimum pressure set value, the intracorporeal microcontroller controls the at least one pump and the solenoid valve set to fill the C-shaped bag of the one of the urethral blockers in the filled state with the liquid.

19. The intracorporeal apparatus according to claim 1, wherein the at least one pump has a flow rate of 3 mL/min-40 mL/min, and the at least one pump has pressure intensity of 5-120 kPa.

20. The intracorporeal apparatus according to claim 1, wherein the intracorporeal apparatus further comprises an intracorporeal wireless transmission module, the intracorporeal microcontroller being electrically connected with the intracorporeal wireless transmission module, the intracorporeal wireless transmission module is configured to obtain electric energy wirelessly from outside of the body and configured for bidirectional wireless communication with an extracorporeal wireless transmission module that is outside of the body, and the extracorporeal wireless transmission module and the intracorporeal wireless transmission module are capable of the bidirectional wireless communication with each other to transmit information.

21. An automatic control system for urinary incontinence with a function of multi-point switching in turn, the automatic control system for urinary incontinence comprising an extracorporeal apparatus adapted to be located outside the body and the intracorporeal apparatus according to claim 1.

22. The automatic control system for urinary incontinence according to claim 21, wherein the extracorporeal apparatus comprises an extracorporeal wireless transmission module, an extracorporeal microcontroller, and a power module, the power module being configured to supply power to the extracorporeal wireless transmission module and the extracorporeal microcontroller, the extracorporeal microcontroller being electrically connected with the extracorporeal wireless transmission module, wherein the extracorporeal wireless transmission module is wirelessly coupled with an intracorporeal wireless transmission module, and the extracorporeal wireless transmission module is configured to transmit electric energy to the intracorporeal wireless transmission module, and the extracorporeal wireless transmission module and the intracorporeal wireless transmission module are capable of bidirectional wireless communication with each other.

23. The automatic control system for urinary incontinence according to claim 21, wherein the extracorporeal apparatus further comprises a display and control module, which is electrically connected with an extracorporeal microcontroller to display operation information of the automatic control system for urinary incontinence and to input operating commands and parameters.

24. The automatic control system for urinary incontinence according to claim 23, wherein the display and control module comprises a touch screen.

25. The automatic control system for urinary incontinence according to claim 21, wherein the extracorporeal apparatus further comprises an alarm module, which is electrically connected with an extracorporeal microcontroller to emit an alarm signal indicating system abnormality to a user.

26. The automatic control system for urinary incontinence according to claim 21, wherein the extracorporeal apparatus further comprises a Bluetooth® communication module and/or a WIFI module, the Bluetooth® communication module and/or the WIFI module being configured to be capable of communicating with a cloud server or a mobile terminal.

* * * * *